(12) United States Patent
Sauter et al.

(10) Patent No.: US 7,110,192 B2
(45) Date of Patent: Sep. 19, 2006

(54) SYSTEM AND METHOD FOR A COMPOSITE LENS FOR A FLOW CYTOMETER

(75) Inventors: Megan Lynne Sauter, Fort Collins, CO (US); Johnathan Charles Sharpe, Hamilton (NZ); Sean B. Pieper, Fort Collins, CO (US)

(73) Assignee: Dako Denmark A/S, Glostrup (DK)

( * ) Notice: Subject to any disclaimer, the term of this patent is extended or adjusted under 35 U.S.C. 154(b) by 50 days.

(21) Appl. No.: 11/033,858

(22) Filed: Jan. 12, 2005

(65) Prior Publication Data

US 2006/0152823 A1    Jul. 13, 2006

(51) Int. Cl.
*G02B 9/00* (2006.01)
*G02B 9/62* (2006.01)

(52) U.S. Cl. ...................... 359/754; 359/756

(58) Field of Classification Search ........ 359/754–756, 359/658, 681, 713; 356/436, 440
See application file for complete search history.

(56) References Cited

U.S. PATENT DOCUMENTS

| | | | |
|---|---|---|---|
| 4,545,677 A | 10/1985 | Chupp | |
| 4,660,971 A | 4/1987 | Sage et al. | |
| 4,673,288 A | 6/1987 | Thomas et al. | |
| 4,710,635 A | 12/1987 | Chupp | |
| 4,786,165 A | 11/1988 | Yamamoto et al. | |
| 4,818,103 A | 4/1989 | Thomas et al. | |
| 4,989,977 A | 2/1991 | North, Jr. | |
| 5,032,381 A | 7/1991 | Bronstein et al. | |
| 5,260,764 A | 11/1993 | Fukuda et al. | |
| 5,350,695 A | 9/1994 | Colella et al. | |
| 5,351,118 A | 9/1994 | Spinell | |
| 5,360,739 A | 11/1994 | Fan et al. | |
| 5,631,730 A | 5/1997 | Chupp et al. | |
| 5,684,575 A | 11/1997 | Steen | |
| 5,739,902 A | 4/1998 | Gjelsnes et al. | |
| 5,872,627 A | 2/1999 | Miers | |
| 5,973,842 A | 10/1999 | Spangenberg | |
| 6,042,249 A | 3/2000 | Spangenberg | |
| 6,097,485 A | 8/2000 | Lievan | |
| 6,177,277 B1 | 1/2001 | Soini | |
| 6,510,007 B1 | 1/2003 | Blasenheim | |
| 6,549,275 B1 | 4/2003 | Cabuz et al. | |
| 6,597,438 B1 | 7/2003 | Cabuz et al. | |
| 6,683,314 B1 * | 1/2004 | Oostman et al. | 250/459.1 |

(Continued)

FOREIGN PATENT DOCUMENTS

EP    0 246 604 A2    11/1987

(Continued)

*Primary Examiner*—Alicia M Harrington
(74) *Attorney, Agent, or Firm*—Dako Global Intellectual Property; Thomas F. Cooney

(57) ABSTRACT

A lens system for collecting and focusing light emanating from an object has a cuvette housing the object and having a wall of thickness not greater than 1.5 millimeters; a plano-convex lens having a planar surface affixed to the wall; a sequence of at least three meniscus lenses, each meniscus lens having a concave surface toward the object and a convex surface, each successive meniscus lens receiving the light from the immediately preceding meniscus lens and having radii of curvature of its concave and convex surfaces greater than corresponding radii of the preceding meniscus lens; and at least one compound lens that may be a doublet lens or a triplet lens, the compound lens receiving the light from a last meniscus lens, wherein an image of a geometrical point on the object has a root-mean square spot size equal to or less than 63 μm.

24 Claims, 3 Drawing Sheets

U.S. PATENT DOCUMENTS

| | | |
|---|---|---|
| 6,700,130 B1 | 3/2004 | Fritz |
| 6,713,019 B1 | 3/2004 | Ozasa et al. |
| 6,813,017 B1 | 11/2004 | Hoffman et al. |
| 6,819,411 B1 | 11/2004 | Sharpe et al. |
| 6,970,245 B1 | 11/2005 | Fritz et al. |
| 2003/0054558 A1 | 3/2003 | Kurabayashi et al. |
| 2003/0142291 A1 | 7/2003 | Padmanabhan et al. |
| 2003/0197945 A1 | 10/2003 | Kurata |
| 2004/0061853 A1 | 4/2004 | Blasenheim |

FOREIGN PATENT DOCUMENTS

| | | |
|---|---|---|
| EP | 0409293 A2 | 1/1991 |
| JP | 2000155267 | 6/2000 |
| JP | 2003161881 | 6/2003 |
| SU | 723 482 A1 | 3/1980 |
| WO | WO 03/019625 A1 | 3/2003 |
| WO | WO 2004/034122 A2 | 4/2004 |

* cited by examiner

SYSTEM AND METHOD FOR A COMPOSITE LENS FOR A FLOW CYTOMETER

FIELD OF THE INVENTION

The present invention relates generally to optical lens systems that are used for studying the interaction of microscopic particles with electromagnetic radiation. More particularly, the present invention relates to an optical lens system for use in a flow cytometer, wherein the lens system captures and transmits scattered light, fluorescence or other electromagnetic radiation to one or more sensing devices.

BACKGROUND OF THE INVENTION

In a flow cytometer, particles of interest (i.e. cells, beads, or other microscopic objects) are transported in a carrier fluid though a cuvette or flow cell. As is well known in the art, some of these particles may be non-fluorescent whereas others may be marked with fluorescent labels that can be used to identify specific particle characteristics or may hold an inherent autofluorescence characteristic which, when excited, can cause emission of electromagnetic radiation (such as photon irradiation or emission).

Lasers are used to excite said labels or particles and signal detection by sensing devices allows parameters such as size, shape, DNA content, surface receptors, enzyme activity, membrane permeability and calcium flux, to name a few applications, to be measured. The present invention is used for signal (where the term "signal" can be considered to pertain to radiation contained within one or more of the UV, visible, or IR regions of the electromagnetic spectrum) collection. The objective lens is typically designed to gather light (scattered, fluorescent, or other) from particles flowing through the interrogation/observation region of the flow cytometer and produce an image that is magnified with respect to the original object. This magnified image may be spatially separated and carried on to be detected by one or more suitable sensing devices such as photomultiplier tubes as those familiar with this technology would appreciate.

Historically, flow cytometers have utilized microscope grade objectives because of the common availability of stock lens parts and designs. Since microscopes are vision systems the optical aberrations are designed to be very low. This insures good quality so that the image can be viewed clearly by the human eye. However, flow cytometers are typically not vision systems and the same amount of image quality has not previously been required to achieve adequate results on a cytometer. The focused image created by the cytometer objective is often formed for simple optical path separation since there may be multiple lasers acting on the stream of particles at one time. It is necessary to maintain a level of quality in the image in order to proceed down the correct respective path and maintain the signal/photons to be detected by the sensing devices. However, this is a lesser level of image quality than what is required when the sensing device is the human eye as is the case in many microscopes.

Specialized optical collection lens systems for flow cytometry that do not rely on commercial microscope objectives have been described. One such prior-art lens system 100 for use in flow cytometry is illustrated in FIG. 1. The lens system 100 (FIG. 1) comprises a transparent plate 108, a plano-convex lens 110 optically coupled to the plate 108, a first meniscus lens 112 optically coupled to the plano-convex lens 110 at a side opposite to the plate 108 and a second meniscus lens 114 optically coupled to the first meniscus lens 112 opposite to the plano-convex lens 110. The prior-art system 100 further comprises a first doublet lens 116 optically coupled to the second meniscus lens 114 at a side opposite to the first meniscus lens 112 and a second doublet lens 122 optically coupled to the first doublet lens 116 as a side opposite to the second meniscus lens 114.

The lens system 100 (FIG. 1) is adapted to magnify the image of and collect light emitted or scattered from an object (OBJ) 102 (typically, biological cellular material) situated within a solution (typically saline water) passing through or housed within a cuvette comprising cuvette walls 104. An optical gel layer 106 provides an interface between the cytometry flow cell and the lens proper and improves lens mounting tolerances.

The plano-convex lens 110 of the prior-art system 100 (FIG. 1) is of a single material of less than 1.55 refractive index and has a planar surface defining an object side of the system and a convex surface having a radius of curvature in a range from 3.5 to 5.5 mm. The two meniscus lenses have concave surfaces facing the object side of the system, the surfaces of the second meniscus lens 114 being less sharply curved than corresponding surfaces of the first meniscus lens 112 and the convex surface of the first meniscus lens 112 being less sharply curved than the convex surface of the plano-convex lens 110.

Although the prior-art flow cytometry lens system 100 is adequate for its intended purposes, it has an overall track length (object to image distance) of over 176 mm and produces a geometrical spot size of 85.04 µm at full field and 71.86 µm on-axis, thereby putting a minimum of 80% of the optical energy of the image of an infinitely small point source within a circle of less than 200 µm diameter. Although a loss in image quality is acceptable for a flow cytometer, it is desirable to have an improved level of resolution for improved signal delivery, optical path separation and spectral resolution. Also, it is desirable to maintain the track length and the lens length (total thickness of all lenses along an optical axis) as small as possible, since space conservation and weight minimization are important considerations in the construction modern flow cytometers. Therefore, the present invention is aimed at improving the resolution and track length relative to the prior art while maintaining a suitable level of chromatic performance. This will allow for greater photon collection and ensure proper delivery of signal to a photo-detection block (comprising a plurality of sensing devices). In particular, a 25% reduction in on-axis and full field RMS spot size is desired with an 80% energy containment radius of 100 µm or less. Numerical aperture should be maximized considering a square cuvette channel to be no less than 0.94. Primary and secondary axial color aberrations should have absolute values less than 0.2 mm.

In addition, the present invention is aimed at reducing the size of the flow cytometer by reducing the overall collection optic track length (as compared to the prior art) by 33%, reducing the lens barrel diameter by over 50% and slightly reducing the lens length. It is desirable to keep the collection optic track length and lens length at less than or equal to 118 mm and 35 mm, respectively, since space and weight conservation are important considerations in the design and construction of today's flow cytometers. In short, the present invention should be physically small with improved resolution and greater chromatic performance as compared to the prior art but should utilize the fact that a cytometer does not need vision quality optics.

SUMMARY OF THE INVENTION

The above mentioned targets are realized with a lens system, disclosed herein, for collecting light from an object housed within a cuvette, wherein the cuvette wall thickness is minimized so that light collection can begin spatially closer to the object. The thin cuvette wall, from 0.75 to 1.50 mm thick, in this system allows for greater light collection while maintaining a small diameter for the ensuing optical elements. A positive plano-convex lens is cemented to the cuvette surface such that the planar surfaces are mated. This lens is approximately hemispherical with the radius of curvature of the lens being similar to its thickness. Following the plano-convex lens is a first group of lenses comprising a series of at least three meniscus lenses all with concave surfaces facing toward the object. The subsequent lenses have a radius of curvature that increases with distance from the object. A final group of lenses optically coupled to the last one of the series of meniscus lenses comprises an achromatic compound lens. In one embodiment, the achromatic compound lens may comprise either a pair of doublet lenses wherein the first doublet lens comprises a biconvex profile and a second doublet lens comprising a concavo-convex profile. In another embodiment, the achromatic compound lens may comprise a triplet lens consisting of a first biconvex lens; a second biconvex lens; and a biconcave lens coupled between the first and second biconvex lenses.

The plano-convex lens in combination with the meniscus lenses collect the maximum amount of light possible with this geometry from the object and collimate it. Since the light being collected from the point source/object is highly divergent, it is necessary to employ a high powered lens configuration. By using multiple meniscus lenses and therefore splitting up the power among the elements, the overall curvature values needed are reduced. By doing so, there is less refraction at each interface which, in turn, reduces the aberrations created in this section of the system. Using smaller radius of curvature values also increases manufacturability. The lenses making up the achromatic compound lens are used to correct for the chromatic aberrations that develop as a result of the preceding elements and to focus the light onto the image plane. Other structures are disclosed in the detailed description below. This summary does not purport to define the invention. The invention is defined by the claims.

BRIEF DESCRIPTION OF THE DRAWINGS

The object and features of the present invention can be more fully understood and better appreciated with reference to the attached drawings, wherein.

DETAILED DESCRIPTION OF THE PREFERRED EMBODIMENTS

The present invention relates to an improved system and method for a composite lens for a flow cytometer. The following description is presented to enable one of ordinary skill in the art to make and use the invention and is provided in the context of a patent application and its requirements. Various modifications to the preferred embodiments will be readily apparent to those skilled in the art and the generic principles herein may be applied to other embodiments. Thus, the present invention is not intended to be limited to the embodiments shown but is to be accorded the widest scope consistent with the principles and features described herein.

Figure 1:
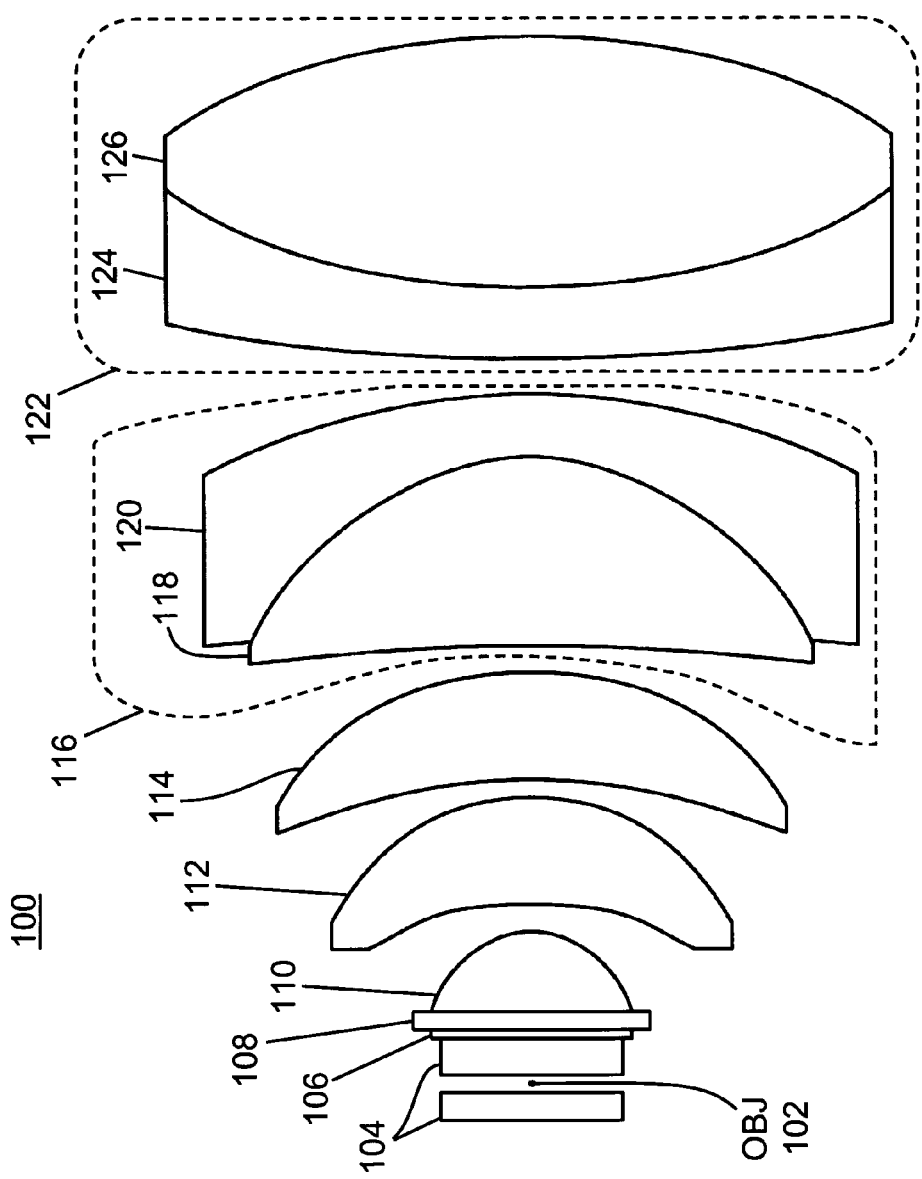
FIG. 1 is a schematic view of the arrangement of lenses and lens surfaces within a prior-art lens system for use in flow cytometry.
Figure 2:
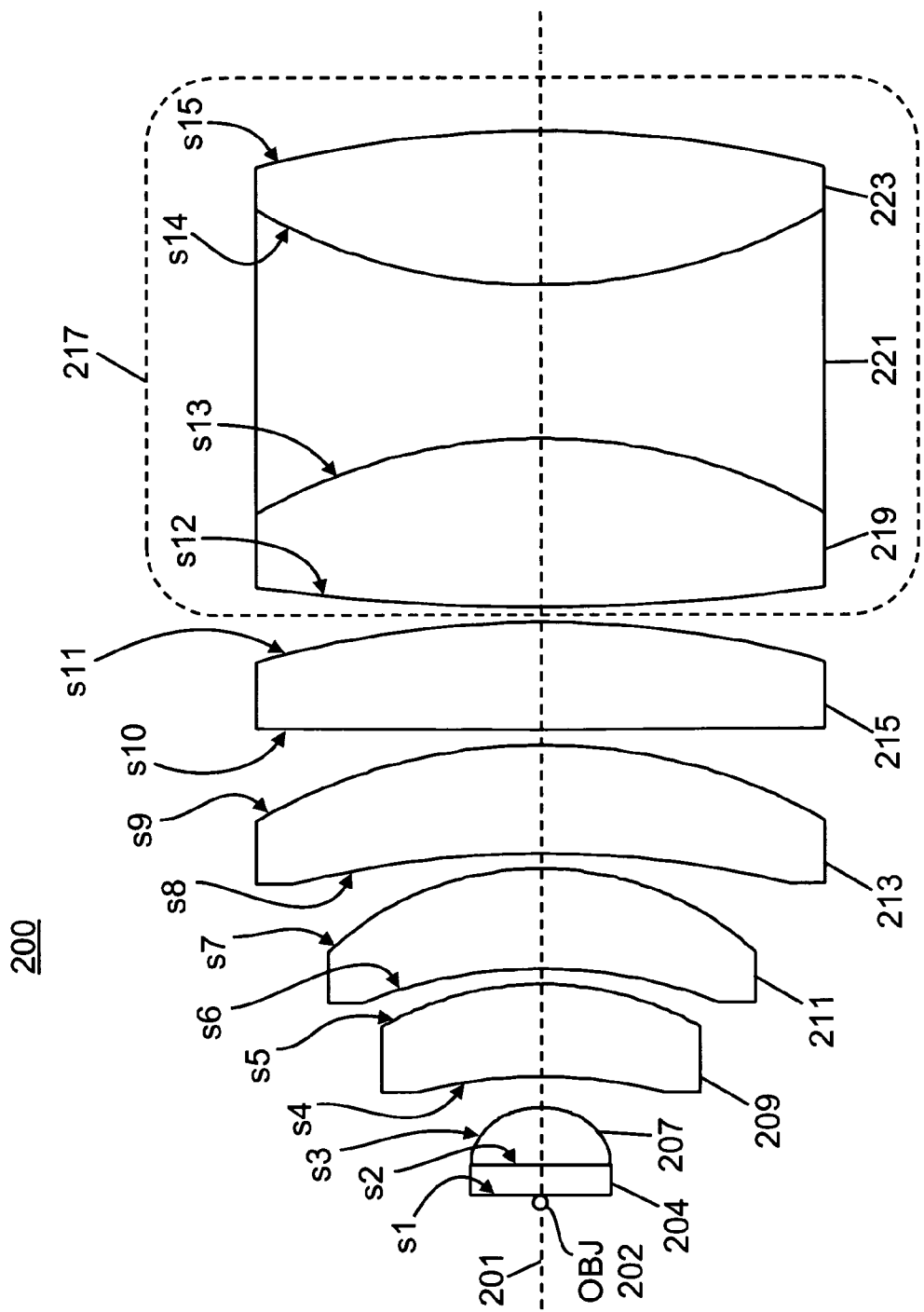
FIG. 2 is a schematic view of the arrangement of lenses and lens surfaces within a first preferred embodiment of a lens system in accordance the present invention.
Figure 3:
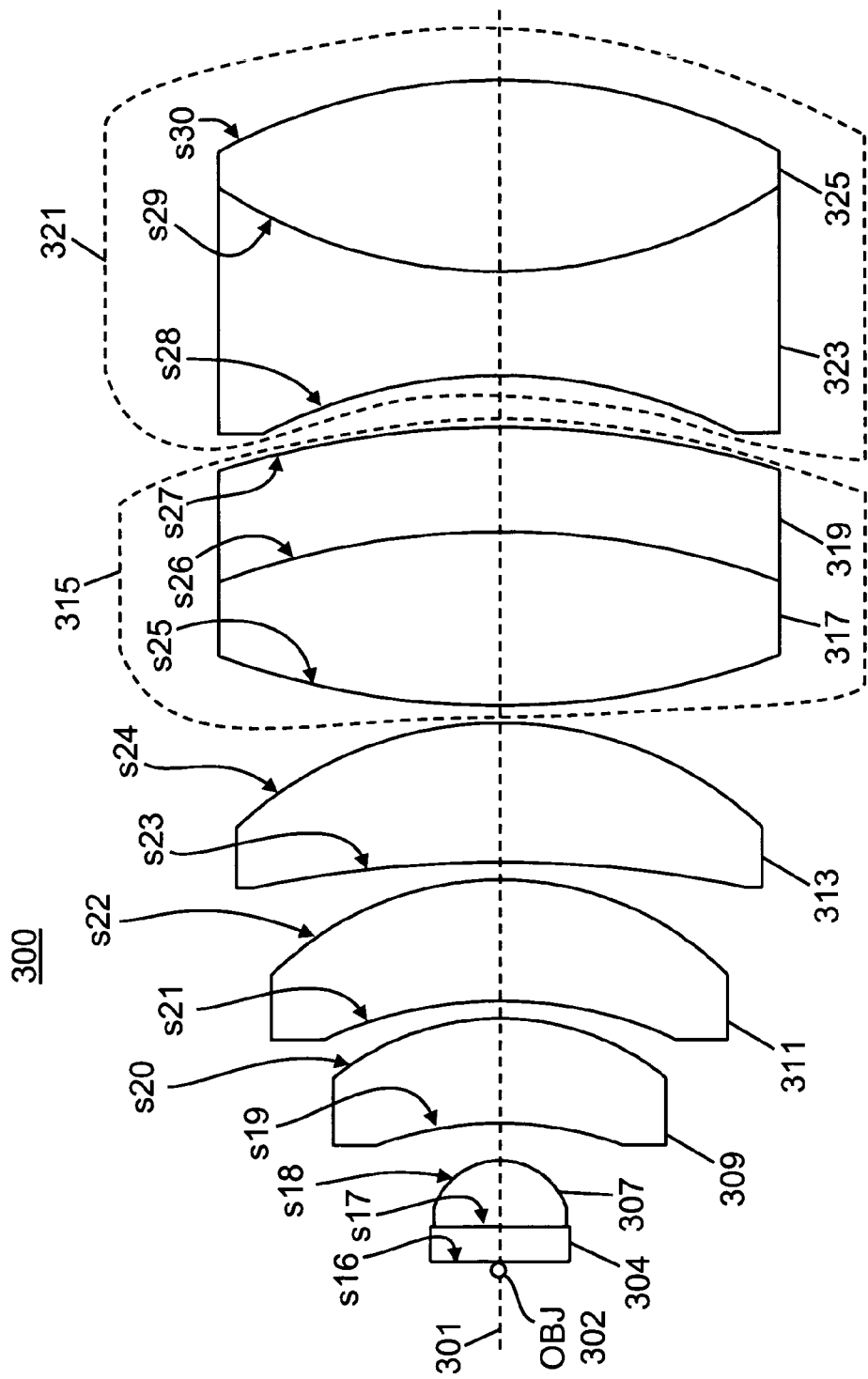
FIG. 3 is a schematic view of the arrangement of lenses and lens surfaces within a second preferred embodiment of a lens system in accordance the present invention.

To more particularly appreciate the features and advantages of the lens system and method of the present invention, the reader is referred to the appended FIGS. 2–3 in conjunction with the following discussion. In both FIG. 2, which illustrates a first preferred embodiment and FIG. 3, which illustrates a second preferred embodiment, reference marks consisting solely of numerals pertain to bulk components (i.e., having mass) whereas reference marks beginning with the letter "s" pertain to surfaces of the bulk components or to interfaces between the bulk components, such interfaces comprising the two mating surfaces of adjacent components.

Preferred Embodiment No. 1

A first preferred embodiment of a cytometry lens system 200 in accordance with the present invention is shown in FIG. 2. The reference marks beginning with the letter "s" in FIG. 2 correspond to the surfaces defined in Table 1. Table 1 contains detailed lens data relating to the preferred embodiment 200. The values of radius of curvature, thickness and aperture provided in Table 1 are in units of millimeters. Entries in the column labeled "Thickness" refer to the distance measured from where the surface in question intersects the axial line 201 (FIG. 2) to where the subsequent surface listed in Table 1 (the surface to the right of the one in question in FIG. 2) intersects this same line. Thus, if the surface in question is on a left side of a lens element (according to the orientation shown in FIG. 2), then the "thickness" entry refers to the thickness of the lens element measured along the axial line 201. If the surface in question is on the right side of a lens element, the "thickness" entry refers to the distance between the lens element and a subsequent surface to its right (according to the orientation shown in FIG. 2) measured along the axial line 201. The one exception pertains to the "thickness" entry for surface s15 which pertains to the distance to the back focal plane (not shown) to the right of the lens system. Entries that pertain to material properties (such as Index of Refraction and Abbe Number) in Table 1 refer to the properties of the material to the right of the surface in question. The refractive indices are shown in relation to the d line ($\lambda$=587.6 nm). The Abbe numbers are shown in relation to the d line ($\lambda$=587.6 nm), the e line ($\lambda$=546.1 nm) and the C line ($\lambda$=643.8 nm).

TABLE 1

| Surface | Radius of Curvature | Thickness | Aperture | Material | Index of Refraction | Abbe Number |
|---|---|---|---|---|---|---|
| OBJ | — | 0.125 | 0.14 | | 1.333 | 42.530 |
| s1 | — | 1.000 | 2.00 | Crown Glass | 1.458 | 50.510 |
| s2 | — | 1.900 | 1.95 | Crown Glass | 1.458 | 50.510 |
| s3 | −2.000 | 1.000 | 3.50 | Air | 1.000 | — |
| s4 | −12.150 | 3.000 | 4.50 | Crown Glass | 1.516 | 47.830 |
| s5 | −8.000 | 0.500 | 5.00 | Air | 1.000 | — |

TABLE 1-continued

| Surface | Radius of Curvature | Thickness | Aperture | Material | Index of Refraction | Abbe Number |
|---|---|---|---|---|---|---|
| s6 | −12.150 | 3.250 | 6.00 | Crown Glass | 1.516 | 47.830 |
| s7 | −8.000 | 0.500 | 7.00 | Air | 1.000 | — |
| s8 | −25.530 | 3.500 | 8.00 | Crown Glass | 1.516 | 47.830 |
| s9 | −14.280 | 0.500 | 8.00 | Air | 1.000 | — |
| s10 | 661.610 | 3.500 | 8.00 | Crown Glass | 1.516 | 47.830 |
| s11 | −25.530 | 0.500 | 8.00 | Air | 1.000 | — |
| s12 | 50.190 | 5.500 | 8.00 | Crown Glass | 1.516 | 47.830 |
| s13 | −14.280 | 5.000 | 8.00 | Flint Glass | 1.673 | 23.240 |
| s14 | 14.280 | 5.000 | 8.00 | Crown Glass | 1.516 | 47.830 |
| s15 | −28.200 | 82.775 | 8.00 | Air | 1.000 | — |

In this embodiment, glass types were chosen for their manufacturing ease, price and availability. The crown glass is modeled after Ohara BSL7 and the flint glass is modeled after Ohara TIM25. Equivalent glasses from different suppliers could be used in this design provided suitable modifications are made to other parameters such as the radius of curvature. One of ordinary skill in the art of lens design would know how to make such modifications to the lens parameters to account for different choices of lens materials. Thus, all such modifications are considered to be within the scope of the present invention. All the lenses defined in the preferred embodiment have spherical surfaces which eases lens manufacture and assembly through alignment tolerance.

Referring to FIG. 2 and the lens data Table 1, the cytometry lens system 200 comprises several optical elements. A thin window (1.00 mm thickness) cuvette wall 204 (bounded by surface s1 on the left and surface s2 on the right, where s1 and s2 are the inner and outer walls of the cuvette, respectively), is a transparent plate that enables a particle 202 (the object "OBJ") to be viewed by the lens system within a flow cytometer. In an effort to collect signal as close to the particle 202 as possible, a near-hemispherical lens 207 is cemented to the cuvette surface with its piano surface s2 facing the object. The lens 207 has an opposite surface s3 with a tight radius of curvature and a thickness similar to the radius of curvature of surface s3. By getting closer to the object with a thin-window cuvette, more light emissions can be collected with a small lens aperture.

In the system 200 (FIG. 2), the plano-convex lens 207 is used in combination with several meniscus lenses to collect the maximum amount of light possible from the object, with this geometry, and collimate this light. Specifically, a first meniscus lens 209 is optically coupled to the right side (that is, the side away from the object 202) of the lens 207, the first meniscus lens being bounded by a concave surface s4 on its left side and a convex surface s5 on its right side. A second meniscus lens 211 is optically coupled to the right side (the side opposite to the object 202) of first meniscus lens 209 and is bounded by a concave surface s6 on its left side and a convex surface s7 on its right side. Similarly, a third meniscus lens 213 is optically coupled to the right side of the second meniscus lens 211 and is bounded by a concave surface s8 on its left side and a convex surface s9 on its right side. Finally, a roughly plano-convex lens 215 is optically coupled to the right side of the third meniscus lens 213, the lens 215 being bounded by a roughly planar (specifically, mildly convex, with a radius of curvature of over 600 mm) surface s10 on its left side and a convex surface s11 on its right side.

The final lens group in the lens system 200 (FIG. 2) is a compound lens that is an achromatic triplet 217 comprising a first bi-convex lens 219 bounded by surfaces s12 and s13, a bi-concave lens 221 cemented to the first biconvex lens 219, the lens 221 bounded by symmetrical surfaces s13 and s14 and a second biconvex lens 223 cemented to the bi-concave lens 221 opposite to the first bi-convex lens and bounded by surfaces s14 and s15. The triplet 217 has an overall biconvex profile with the refractive index of the bi-concave lens 221 being less than the refractive indices of the outer lenses 219 and 223. This triplet lens 217 is used to correct for the chromatic aberrations that develop as a result of the elements 204–215 in the system and to focus the light onto the image plane.

Since the light being collected from the point source/object is highly divergent, it is necessary to employ a high powered lens configuration, which is accomplished by the series of four lenses 209–215. Each of the latter three lenses 211–215 has surfaces with radii of curvature that are the same or larger than the radii of curvature of corresponding surfaces of the respective preceding meniscus lens (that is, the lens to the left of the lens in question). By using multiple meniscus lenses 209–213 and a roughly plano-convex lens 215, the optical lens power is split among these four lens elements, thereby reducing the overall curvature of any individual lens. By minimizing the radii of curvature, there is less refraction at each interface (thus reducing the aberrations created in this section of the system) and improved manufacturability. The use of the plano-convex lens 207 in combination with the series of lenses 209–215 permits the collection of the maximum amount of light from the object and collimation of this light.

It has been found that the lens system 200 produces a maximum spot size at full field of 62.33 μm. The encircled energy radius that contains 80% of the energy is 85.76 μm and will be no greater than 100 μm. It is desired that numerical aperture be maximized when considering a square cuvette channel. This equates to a NA of 0.94 which is achieved by the lens system 200. Further, it is desired that primary and secondary axial color aberrations should have absolute values less than 0.2 mm. This is an important specification since cytometry lenses are typically used from 380 nm to 800 nm. It has been found that the lens system 200 has absolute values of 0.0634 mm and 0.1741 mm for the primary and secondary axial color aberrations respectively.

As far as other parameters are concerned, the small track length of the system (object to image) has been achieved without decreasing the back focal length significantly. This is to minimize the overall size of the flow cytometer instrument. The lens system 200 maintains a short track length of less than 118 mm and has a back focal length of 82.775 mm. This translates to a small lens length of 34.775 mm as well as a maximum lens diameter of 16 mm. These physical aspects in combination prove to be very advantageous for using the lens system within a small cytometer. A certain magnification had to be maintained in this short distance so that different signals could be spatially separated and detected. The system 200 has a magnification in excess of 13×.

Preferred Embodiment No. 2

A second preferred embodiment of a cytometry lens system 300 in accordance with the present invention is shown in FIG. 3. The reference marks beginning with the letter "s" in FIG. 3 correspond to the surfaces defined in Table 2. Other parameters listed in Table 2 are defined similarly to the respective parameters in Table 1, as already discussed above.

TABLE 2

| Surface | Radius of Curvature | Thickness | Aperture | Material | Index of Refraction | Abbe Number |
|---|---|---|---|---|---|---|
| OBJ | — | 0.125 | 0.14 | | 1.333 | 42.530 |
| s16 | — | 1.000 | 2.00 | Crown Glass | 1.458 | 50.510 |
| s17 | — | 1.900 | 1.90 | Crown Glass | 1.458 | 50.510 |
| s18 | −2.000 | 1.068 | 1.90 | Air | 1.000 | — |
| s19 | −10.000 | 3.000 | 3.50 | Crown Glass | 1.516 | 47.830 |
| s20 | −7.500 | 0.500 | 4.50 | Air | 1.000 | — |
| s21 | −12.000 | 3.500 | 5.00 | Crown Glass | 1.516 | 47.830 |
| s22 | −9.110 | 0.500 | 6.50 | Air | 1.000 | — |
| s23 | −34.500 | 4.000 | 7.00 | Crown Glass | 1.516 | 47.830 |
| s24 | −10.900 | 0.500 | 7.50 | Air | 1.000 | — |
| s25 | 23.000 | 5.000 | 8.00 | Crown Glass | 1.516 | 47.830 |
| s26 | −23.000 | 3.000 | 8.00 | Flint Glass | 1.689 | 22.480 |
| s27 | −26.400 | 1.500 | 7.50 | Air | 1.000 | — |
| s28 | −14.360 | 3.000 | 8.00 | Flint Glass | 1.689 | 40.221 |
| s29 | 14.360 | 5.500 | 6.75 | Crown Glass | 1.519 | 22.480 |
| s30 | −16.584 | 83.456 | 8.00 | Air | — | — |

Referring to FIG. 3 and the lens data Table 2, the cytometry lens system 300 comprises several lens elements. A thin window (1.00 mm thickness) cuvette wall 304 (bounded by surface s16 on the left and surface s17 on the right, where s16 and s17 are the inner and outer walls of the cuvette, respectively), is a transparent plate that enables a particle 302 (the object "OBJ") to be viewed by the lens system within a flow cytometer. A near-hemispherical lens 307 is cemented to the cuvette surface with its plano surface s17 facing the object. The lens 307 has an opposite surface s18 with a tight radius of curvature and a thickness similar to the radius of curvature of surface s18. As in the system 200 already described, the use of a thin-window cuvette permits greater light emission to be collected with a small lens aperture.

In the system 300 (FIG. 3), the plano-convex lens 307 is used in combination with a set of three meniscus lenses 309–313 to collect the maximum amount of light possible from the object, with this geometry, and collimate this light. Specifically, a first meniscus lens 309 is optically coupled to the right side (that is, the side away from the object 302) of the lens 307, the first meniscus lens being bounded by a concave surface s19 on its left side and a convex surface s20 on its right side. A second meniscus lens 311 is optically coupled to the right side of the first meniscus lens 309 and is bounded by a concave surface s21 on its left side and a convex surface s22 on its right side. Similarly, a third meniscus lens 313 is optically coupled to the right side of the second meniscus lens 311 and is bounded by a concave surface s23 on its left side and a convex surface s24 on its right side. Each of the latter two meniscus lenses 311–313 has surfaces with radii of curvature that are the same or larger than the radii of curvature of corresponding surfaces of the respective preceding meniscus lens (that is, the lens to the left of the lens in question). As previously described with reference to the lens system 200, the use of the multiple meniscus lenses 309–313 provides a high power system while permitting the optical lens power to be split among these three lens elements, thereby minimizing aberrations and improving manufacturability.

A first compound lens, doublet lens 315, comprising a bi-convex lens 317 and a meniscus lens 319 cemented to the bi-convex lens 317, is optically coupled to the right side of the third meniscus lens 313. This first doublet lens 315 has an overall bi-convex profile. Finally, a second compound lens, doublet lens 321, comprising a bi-concave lens 323 cemented to a bi-convex lens 325, is optically coupled to the first doublet 315. The second doublet lens 321 has an overall concave-convex profile. The pair of doublet lenses 315 and 321 are used to correct for the chromatic aberrations that developed as a result of the first elements in the system and to focus the light onto the image plane.

Since the light being collected from the point source/object is highly divergent, it is necessary to employ a high powered lens configuration, which is accomplished by the series of four lenses 209–215, thereby reducing the overall curvature of any individual lens. By minimizing the radii of curvature, there is less refraction at each interface, thus reducing the aberrations created in this section of the system and improving manufacturability. The use of the plano-convex lens 207 in combination with the series of lenses 209–215 permits the collection of the maximum amount of light from the object and collimation of this light.

The lens system 300 (FIG. 3) has a maximum spot size at full field of 54.48 μm with an encircled energy radius that contains 80% of the energy of 71.62 μm and that will be no greater than 100 μm. As with the lens system 200, the NA is 0.94. The lens system 300 has absolute values of 0.0021 mm and 0.1365 mm for the primary and secondary axial color aberrations, respectively, a short track length of less than 118 mm and a back focal length of 83.456 mm. This translates to a small lens length of 34.093 mm as well as a maximum lens diameter of 16 mm. The lens system 300 has a magnification in excess of 13×.

An improved lens system for a flow cytometer has been disclosed. Those skilled in the art can now appreciate, from the foregoing description, that the broad techniques of the embodiments of the present invention can be implemented in a variety of forms. Therefore, while the embodiments of this invention have been described in connection with particular examples thereof, the true scope of the embodiments of the present invention should not be so limited since other modifications, whether explicitly provided for or implied by this specification, will become apparent to the skilled artisan upon a study of the drawings, specification and following claims.

What is claimed is:

1. A lens system for collecting and focusing light emanating from an object comprising:
   a cuvette housing the object and having a wall of thickness not greater than 1.5 millimeters;
   a plano-convex lens having a planar surface affixed to the wall;
   a sequence of at least three meniscus lenses, each meniscus lens having a concave surface toward the object and a convex surface, a first one of the meniscus lenses receiving the light from the plano-convex lens, each successive meniscus lens receiving the light from the immediately preceding meniscus lens and having radii of curvature of its concave and convex surfaces greater than corresponding radii of the preceding meniscus lens; and at least one compound lens chosen from the group consisting of a doublet lens and a triplet lens, the compound lens receiving the light from a last one of the meniscus lenses, wherein an image of a geometrical point on the object has a root-mean square spot size equal to or less than 63 μm.

2. The lens system of claim 1, wherein 80% of the energy of the image is contained within a circle of radius no greater than 100 μm.

3. The lens system of claim 1, wherein primary and secondary axial color aberrations have absolute values less than 0.2 mm.

4. The lens system of claim 1, wherein the magnification is greater than 13×.

5. The lens system of claim 1, wherein the plano-convex lens has a convex surface with a radius of curvature that is not more than 5.3% greater than the thickness of the plano-convex lens.

6. The lens system of claim 1, wherein the light collection numerical aperture is not less than 0.94.

7. The lens system of claim 1, wherein the image has a root-mean square spot size equal to or less than 55 μm.

8. The lens system of claim 7, wherein 80% of the energy of the image is contained within a circle of radius no greater than 86 μm.

9. The lens system of claim 1, wherein a compound lens of the at least one compound lens is a first doublet lens having a bi-convex profile receiving the light from the last one of the meniscus lenses, wherein said lens system further comprises a second doublet lens having a concavo-convex profile, a concave surface of the second doublet lens receiving the light from the first doublet lens.

10. The lens system of claim 9, wherein the first doublet lens comprises a crown glass biconvex lens and a flint glass meniscus lens and wherein the second doublet lens comprises a flint glass biconcave lens and a crown glass biconvex lens.

11. The lens system of claim 10, wherein the material of the cuvette, the plano-convex lens and each one of the meniscus lenses is crown glass.

12. The lens system of claim 1, wherein an object to image distance is less than or equal to 118 mm.

13. The lens system of claim 1, further comprising another lens chosen from the group consisting of a bi-convex lens and a plano-convex lens optically coupled between the last one of the meniscus lenses and the at least one compound lens.

14. The lens system of claim 13, wherein the at least one compound lens is a triplet lens consisting of:
a first biconvex lens;
a second biconvex lens; and
a biconcave lens coupled between the first and second biconvex lenses.

15. The lens system of claim 14, wherein the material of the first and second biconvex lenses is crown glass and the material of the biconcave lens is flint glass.

16. The lens system of claim 14, wherein the material of the plano-convex lens, each one of the meniscus lenses and the other lens is crown glass.

17. A method for collecting and focusing light emanating from an object comprising:
housing the object within a cuvette having a wall of thickness not greater than 1.5 millimeters;
passing the light through a plano-convex lens having a planar surface affixed to the wall;
passing the light, in sequence, through a group of at least three meniscus lenses, each meniscus lens having a concave surface toward the object and a convex surface, a first one of the meniscus lenses receiving the light from, the plano-convex lens, each successive meniscus lens receiving the light from the immediately preceding meniscus lens and having radii of curvature of its concave and convex surfaces greater than corresponding radii of the preceding meniscus lens; and
passing the light through at least one compound lens chosen from the group consisting of a doublet lens and a triplet lens, the compound lens receiving the light from a last one of the meniscus lenses, wherein the lenses are chosen so as to produce an image of a geometrical point on the object that has a root-mean square spot size equal to or less than 63 μm.

18. The method of claim 17, wherein 80% of the energy of the image is contained within a circle of radius no greater than 100 μm.

19. The method of claim 17, wherein primary and secondary axial color aberrations have absolute values less than 0.2 mm.

20. The method of claim 17, wherein the magnification greater than 13×.

21. The method of claim 17, wherein the plano-convex lens has a convex surface with a radius of curvature that is not more than 5.3% greater than the thickness of the plano-convex lens.

22. The method of claim 17, wherein the light collection numerical aperture is not less than 0.94.

23. The method of claim 17, wherein an object to image distance is less than or equal to 118 mm.

24. The method of claim 17, wherein the image has a root-mean square spot size equal to or less than 55 μm.

* * * * *